(12) United States Patent
Lucchini et al.

(10) Patent No.: US 12,390,323 B2
(45) Date of Patent: Aug. 19, 2025

(54) BONE ANCHOR FOR ATTACHING A SUTURE THREAD OR LIGAMENT

(71) Applicant: MEDACTA INTERNATIONAL SA, Castel San Pietro (CH)

(72) Inventors: Riccardo Lucchini, Castel San Pietro (CH); Sascha Berberich, Castel San Pietro (CH); Francesco Siccardi, Castel San Pietro (CH); Matteo Ferrari, Castel San Pietro (CH); Matteo Ponzoni, Castel San Pietro (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 58 days.

(21) Appl. No.: 17/275,124

(22) PCT Filed: Aug. 23, 2019

(86) PCT No.: PCT/IB2019/057101
§ 371 (c)(1),
(2) Date: Mar. 10, 2021

(87) PCT Pub. No.: WO2020/053686
PCT Pub. Date: Mar. 19, 2020

(65) Prior Publication Data
US 2022/0031445 A1 Feb. 3, 2022

(30) Foreign Application Priority Data
Sep. 11, 2018 (IT) .......................... 102018000008480

(51) Int. Cl.
*A61F 2/08* (2006.01)

(52) U.S. Cl.
CPC ..... *A61F 2/0811* (2013.01); *A61F 2002/0858* (2013.01); *A61F 2002/0888* (2013.01); *A61F 2220/0075* (2013.01)

(58) Field of Classification Search
CPC ............ A61F 2/0811; A61F 2002/0858; A61F 2002/0852; A61F 2002/0888;
(Continued)

(56) References Cited

U.S. PATENT DOCUMENTS

2002/0161401 A1* 10/2002 Steiner .................. A61B 17/04
2002/0188305 A1* 12/2002 Foerster et al. ...... A61F 2/0811
(Continued)

FOREIGN PATENT DOCUMENTS

WO 2007024282 A2 3/2007
WO 2010014825 A1 2/2010

OTHER PUBLICATIONS

International Search Report and Written Opinion for International Application No. PCT/IB2019/057101 dated Nov. 12, 2019, 15 pages.

*Primary Examiner* — Julian W Woo
*Assistant Examiner* — Bridget E. Rabaglia
(74) *Attorney, Agent, or Firm* — Meunier Carlin & Curfman LLC

(57) ABSTRACT

A bone anchor for attaching a suture thread or ligament comprises a main body extending along a longitudinal axis and having a fork-shaped end portion. The end portion is provided with a first and a second fork arm each extending between a constrained end and a free end and spaced apart by an axial slit for receiving a suture thread. Said first and second fork arms have, at their constrained ends, a transverse notch defining two axial retention shoulders for the suture thread.

7 Claims, 4 Drawing Sheets

(58) Field of Classification Search
CPC ..... A61F 2220/0075; A61B 2017/0414; A61B 17/0401; A61B 2017/0412; A61B 2017/0438; A61B 17/58; A61B 17/864; A61B 2017/044; A61B 2017/0648
See application file for complete search history.

(56) References Cited

U.S. PATENT DOCUMENTS

| | | | |
|---|---|---|---|
| 2005/0080455 A1* | 4/2005 | Schmieding et al. | ........................ A61B 17/0401 |
| 2013/0103081 A1* | 4/2013 | Wolf | .................. A61B 17/0401 |
| 2013/0158599 A1* | 6/2013 | Hester | ................ A61B 17/0401 606/232 |
| 2016/0007994 A1* | 1/2016 | Park | .................. A61B 17/0401 |
| 2016/0128685 A1* | 5/2016 | Hester | ................ A61B 17/0401 |
| 2020/0000574 A1* | 1/2020 | Khowaylo et al. | ... A61F 2/0811 |

* cited by examiner

BONE ANCHOR FOR ATTACHING A SUTURE THREAD OR LIGAMENT

TECHNICAL FIELD

The present invention relates to a bone anchor for attaching a suture thread or ligament.

The present invention is therefore applicable in the surgical field, in particular in the field of arthroscopic surgery, as a device for the attachment (permanent or temporary) of suture threads or ligaments to a patient's bone support.

BACKGROUND ART

In the prior art, devices are known of, called "anchors", which are used by the surgeon when it is necessary to secure soft tissues, previously removed or moved, to the patient's bone.

Such anchors are generally defined by small plugs having a first end, provided with a slit for receiving the suture thread, and a second end couplable to a handling device.

In particular, in the anchors currently on the market, the first end is actually defined by a fork inside which the surgeon can insert the suture thread, which, once brought into a position suitable for attachment, is inserted under pressure inside a hole, or milling, suitably made in the bone.

More precisely, the suture thread is forked by the surgeon in an easily accessible or visible area and subsequently the anchor is made to slide along the thread until the aforementioned "suitable position" is reached.

At this point, the anchor is inserted into the hole together with the suture thread (or ligament) and the related soft tissue attached to it is constrained to the bone.

However, the working environment during arthroscopic surgery is usually very "disturbed", both due to the presence of numerous tissues to be removed/moved and due to the presence of fluids, both bodily and injected at the site of surgery (e.g. saline solution), making it difficult to handle the suture thread.

In particular, the presence of fluids of various kinds tends to make the suture thread fluctuate making it difficult to grasp and, above all, difficult to retain during the sliding of the anchor along it.

This clearly translates into an increase in surgery times and considerable stress on the part of the surgeon who, at the end of the surgery, encounters difficulties at a stage of the operation that should be straightforward.

DISCLOSURE OF THE INVENTION

The object of the present invention is therefore to provide a bone anchor for attaching a suture thread or ligament that is capable of overcoming the drawbacks of the aforementioned known art.

In particular, the object of the present invention is to provide a bone anchor for attaching a suture thread or ligament that is easy to handle and which facilitates the retention of the suture thread (or ligament).

Said purposes are achieved by a bone anchor for fixing a suture thread or ligament having the technical characteristics of one or more of the following claims.

In particular, such purposes are achieved by a bone anchor for attaching a suture thread or ligament comprising a main body extending along a longitudinal axis and having a fork-shaped end portion.

The end portion is provided with a first and second fork arms each extending between a constrained end and a free end and spaced apart by an axial slit for receiving a suture thread.

According to one aspect of the invention, the first and second fork arms have, at their constrained ends, a transverse notch defining two axial retention shoulders for said suture thread.

Advantageously, in this way the surgeon can retain the suture thread inside the slit simply by forking the thread between the fork arms and rotating the anchor around its longitudinal axis.

This rotation, with an effect similar to a bayonet, involves the positioning of the thread inside at least one of the transverse notches, the retention shoulders of which oppose the axial movement (and therefore escape) of the thread.

Preferably, the first and second arm have an "L" or "J" conformation. The area above the base of the "L" or the hook of the "J" thus corresponds to the transverse notch.

Preferably, the first and second arms each have an extension transverse to the longitudinal axis delimited by a first and a second side edge.

The arms are positioned so that the first side edges and the second side edges are facing each other.

Preferably, the transverse notch of the first arm extends from the first side edge in the direction of the second one, while the transverse notch of the second arm extends from the second side edge in the direction of the first one.

Thus, the two fork arms are arranged substantially in polar symmetry with respect to the longitudinal axis. In other words, the two fork arms have opposing "L" or "J" shapes, i.e. with reverse orientation.

Advantageously, in this way, with a single rotation of the anchor around its longitudinal axis, the suture thread fits into both transverse notches, enclosing both arms.

BRIEF DESCRIPTION OF DRAWINGS

These and other features together with their advantages will become clearer from the following exemplary, and therefore non-limiting, description of a preferred, and therefore non-exclusive, embodiment of a bone anchor for attaching a suture thread or ligament as illustrated in the attached drawings, wherein.

DETAILED DESCRIPTION OF PREFERRED EMBODIMENTS OF THE INVENTION

Figure 1:
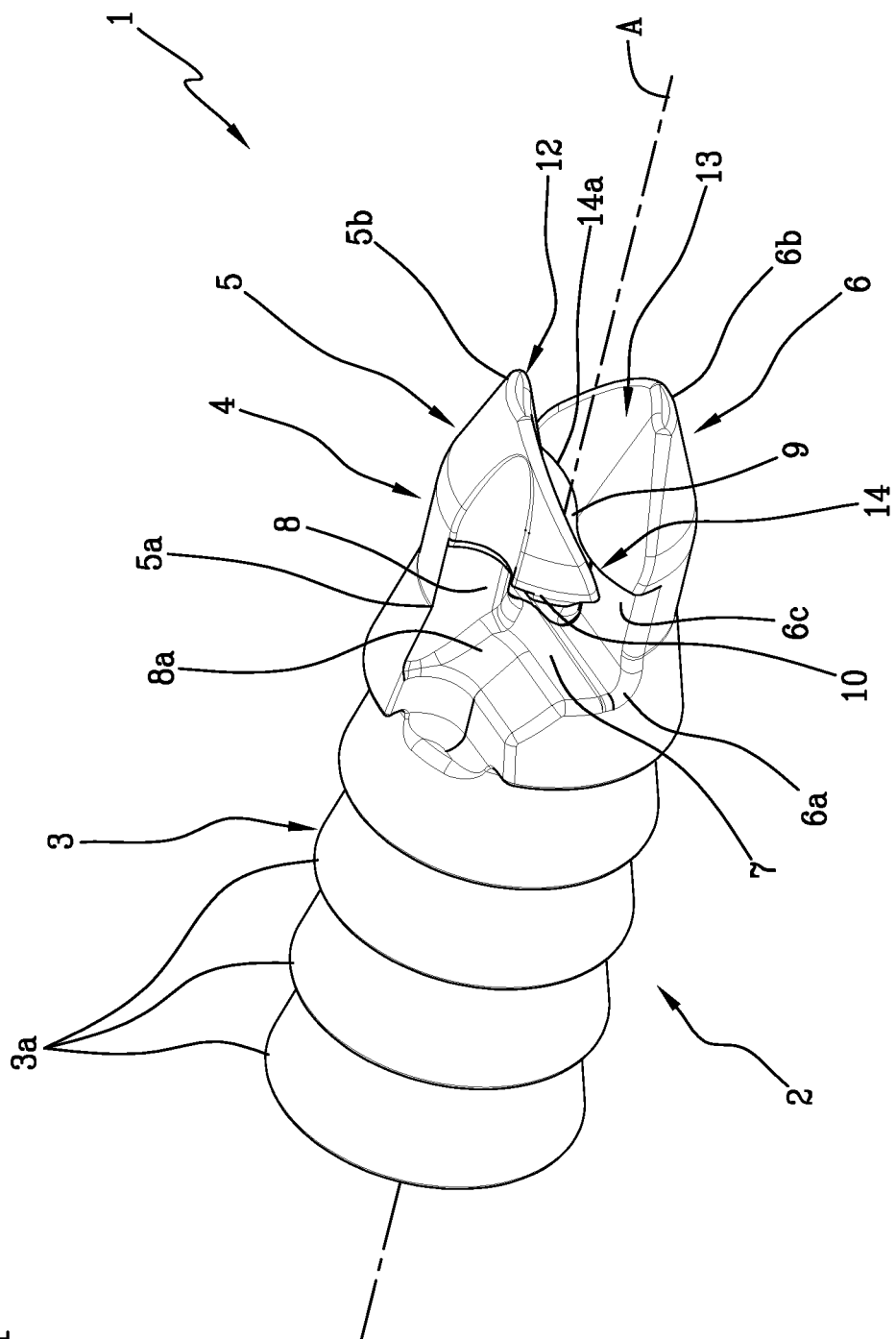
FIGS. 1 and 2 show two perspective views of a bone anchor for attaching a suture thread or ligament according to the present invention.
Figure 2:
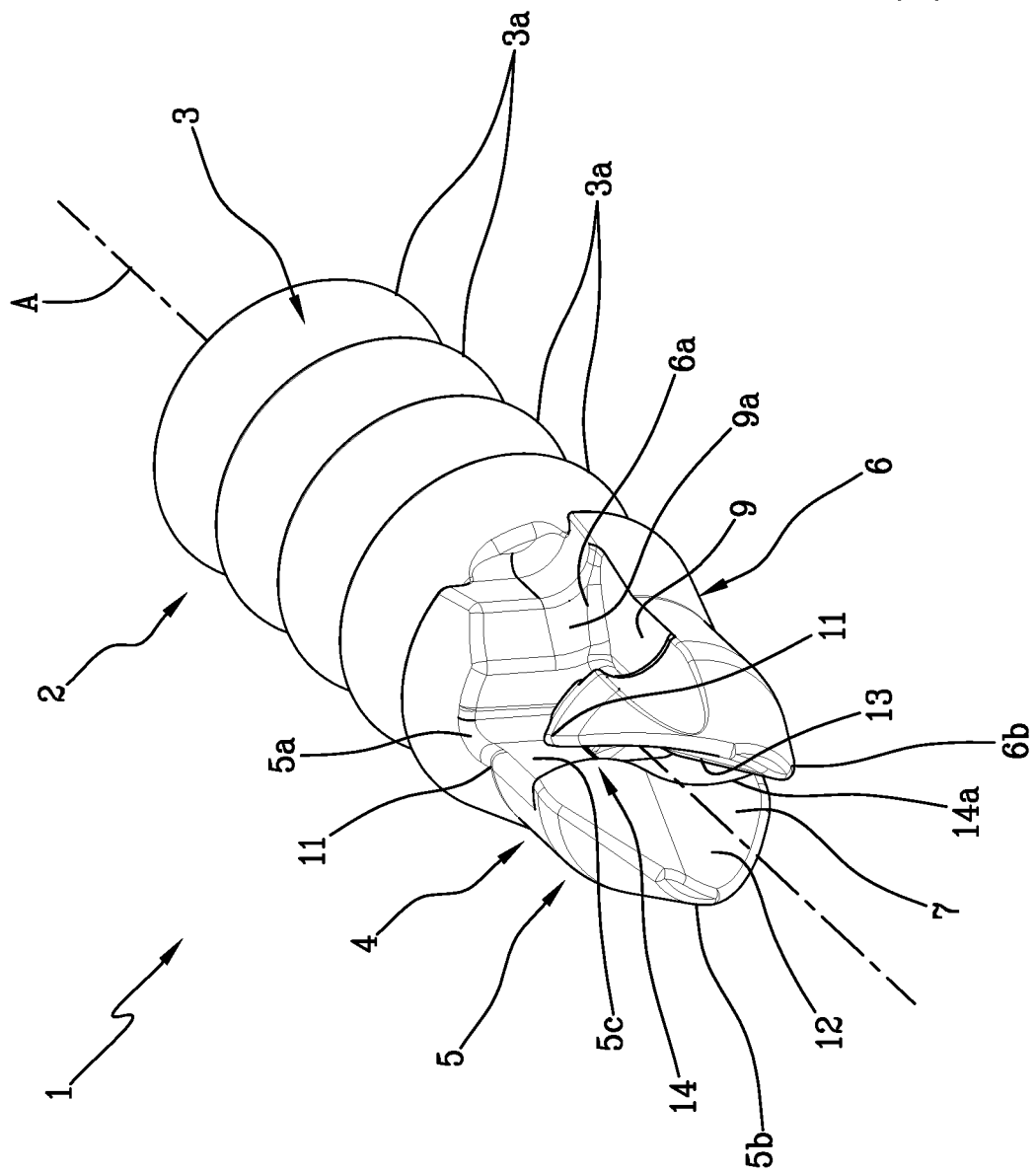
Figure 3:
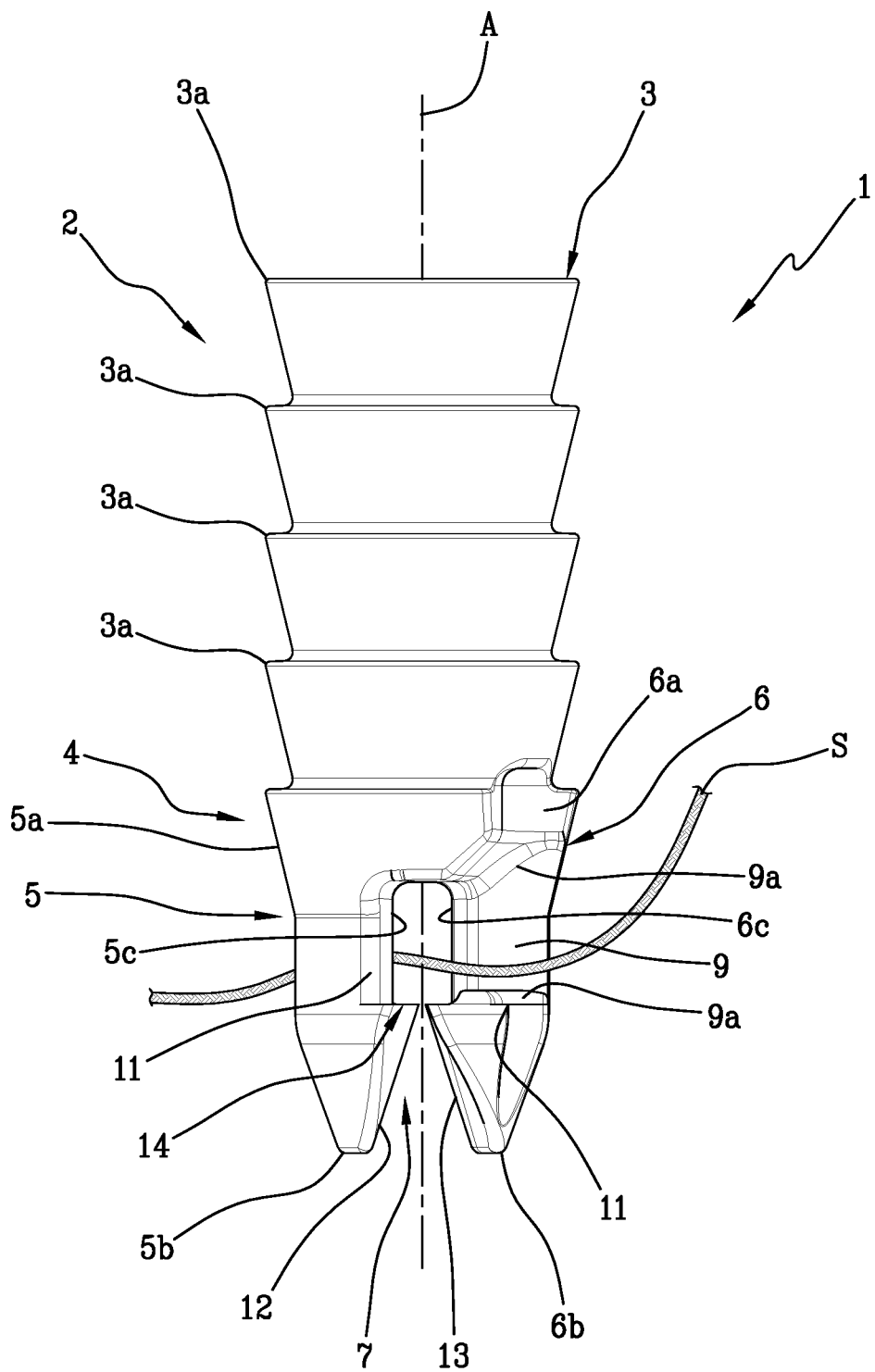
FIGS. 3 and 4 show two 90° offset side views of the bone anchor in FIGS. 1 and 2.
Figure 4:
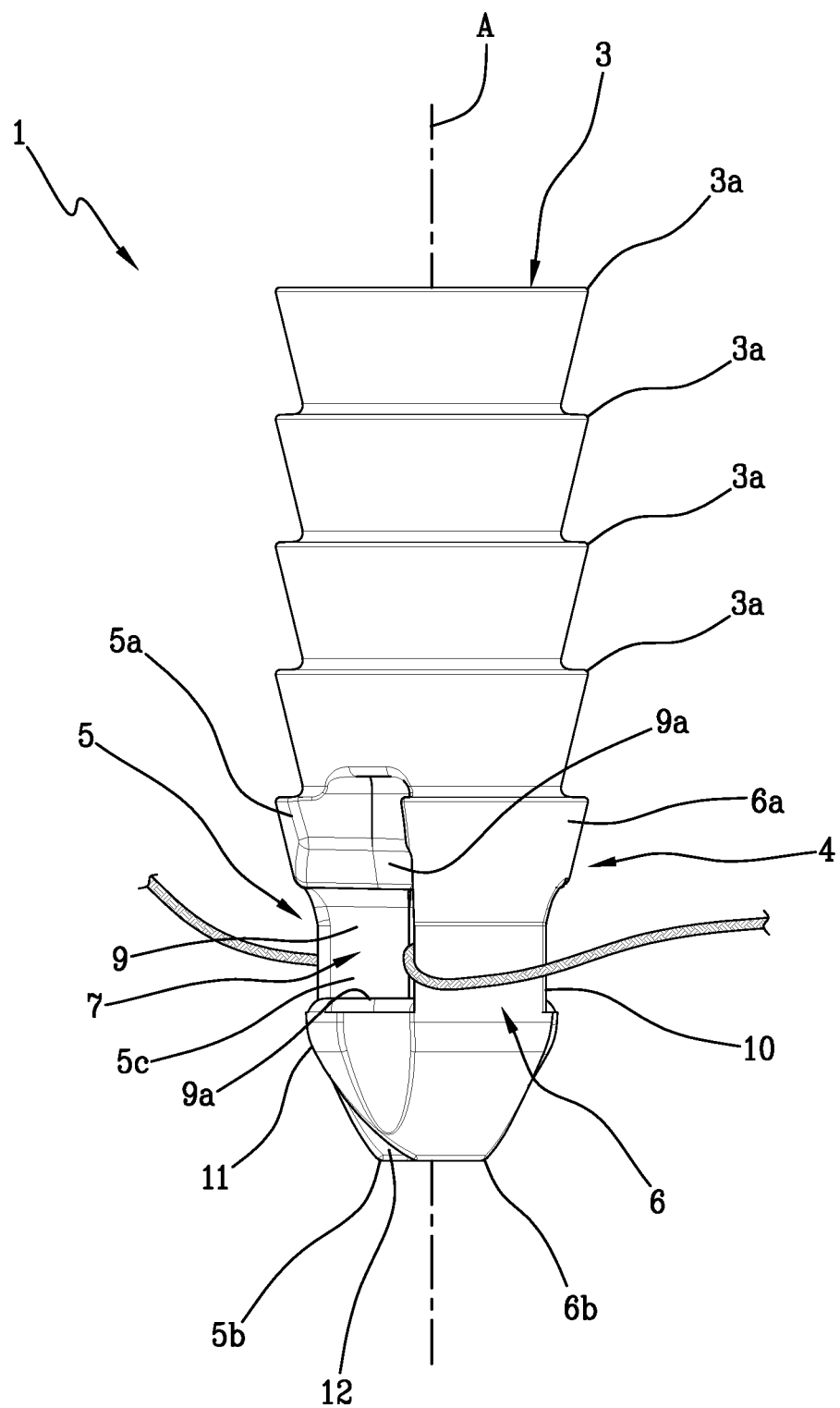

With reference to the attached figures, reference numeral 1 denotes a bone anchor for attaching a suture thread "S" or ligament according to the present invention.

Such an anchor is used, as mentioned, to secure a soft tissue to a bone of a patient by means of an anchoring device comprising a handling member comprising a handle and a handling rod extending along its own main direction, to the free end of which the anchor 1 is removably attached. The anchor 1 comprises a main body 2 extending along a longitudinal axis "A".

The main body 2 is made of PEEK (polyether ether ketone) in order to allow it to be grafted into a patient's bone.

The main body 2 extends along its longitudinal axis "A" between an anchoring portion 3 and an end portion 4.

The anchoring portion 3 and the end portion 4 are thus arranged sequentially (and aligned) along said longitudinal axis "A".

The anchoring portion 3 has a peripheral profile provided with a plurality of clamping elements 3a arranged in succession along said longitudinal axis "A".

In other words, along a radial periphery (relative to the longitudinal axis "A") of the anchoring portion 3 there is a plurality of clamping elements 3a facing away from the longitudinal axis to anchor, by interference or friction, to the side walls of a hole or milling made in the patient's bone.

Such clamping elements 3a are preferably distributed along the longitudinal axis "A" so as to distribute the retaining action of the anchor 1 over multiple points and adapt the anchor 1 to holes of varying depths.

In the preferred embodiment, the anchoring portion 3 has a substantially cylindrical extension along the longitudinal axis "A" with a peripheral sawtooth profile, wherein each tooth defines a clamping member 3a.

In addition, the anchoring portion 3 has an end section that can be coupled with a handling device. In the preferred embodiment, the end section of the anchoring portion 3 has an axial opening that can be coupled with a pin of the handling device, but alternatively the coupling systems with such a device could be of another type, known in themselves.

The end portion 4 of the main body 2 extends along the longitudinal axis "A" from the anchoring portion 3, with which it is preferably made in one piece. 10

The end portion 4 is provided with a first 5 and a second fork arm 6 each extending between a constrained end 5a, 6a and a free end 5b, 6b.

The constrained end 5a, 6a of each fork arm 5, 6 is preferably to be understood as constrained to the anchoring portion 3 of the main body 2 (or in any case to a further portion of such main body). 15

Such first 5 and second arm 6 define a fork structure and are thus spaced apart by an axial slit 7 for receiving the suture thread "S".

In other words, the first 5 and the second fork arm 6 are facing each other and spaced along a first direction, orthogonal to the longitudinal axis "A", so that along a second direction, orthogonal to the first and to the longitudinal axis "A", a through lumen is defined, defining the slit 7. Said through lumen, in use, is passed through by the suture thread "S" when the surgeon "forks" it.

According to one aspect of the invention, the first 5 and the second 6 fork arms have, at their constrained ends 5a, 6a, a transverse notch 8, 9, defining in each arm 5, 6 two axial retention shoulders 8a, 9a for the suture thread "S".

In other words, each arm 5, 6, extending longitudinally, has a transverse (or circumferential) notch that determines, at the constrained end 5a, 6a a restriction or portion of reduced width.

Thus, the first 5 and the second arms 6 have, from the constrained end 5a, 6a to the free end 5b, 6b, an "L" or "J" conformation.

More precisely, the stem of the "L" or "J" corresponds to the restriction, while the base corresponds to the free end 5a, 6b of the first 5 or second arm 6.

It is to be noted that the first 5 and the second arm 6 each extend transversely to the longitudinal axis (i.e. along said second direction) between a first 10 and a second side edge 11.

The fork arms 5, 6 are positioned so that the first side edges 10 and the second side edges 11 are facing each other.

In other words, the first edge 10 of the first arm 5 is aligned (along said first direction) with the first edge 10 of the second arm 6 and the second edge 11 of the first arm 5 is aligned with the second edge 11 of the second arm 6.

According to a preferred aspect of the present invention, the transverse notch 8 of the first arm 5 extends from the first side edge 10 in the direction of the second one 11 and the transverse notch 9 of the second arm 6 extends from the second side edge 11 in the direction of the first one 10.

In other words, by defining an annular travel direction around the longitudinal axis "A", the first 5 and the second fork arm 6 have an orientation concurrent with said direction.

More specifically, the two fork arms 5, 6 are arranged substantially in polar symmetry with respect to the longitudinal axis "A".

Advantageously, in this way with a single rotation of the anchor around its longitudinal axis "A" by the surgeon, the suture thread "A" is inserted into both transverse notches 8, 9, enclosing both arms 5, 6.

Moreover, this conformation causes the suture thread "S" to assume, inside the axial slit 7, a wavy (or S-shaped) pattern, which facilitates axial retention.

In the preferred embodiment, the first 5 and the second arm 6 have respective radially internal walls 5c, 6c facing each other to delimit said axial slit 7.

The radially internal walls 5c, 6c are both provided with respective inclined end walls 12, 13 extending away from each other.

Such inclined end walls 12, 13 thus define a flare or a guide for the suture thread "S" to lodge in the slit 7.

In the preferred embodiment, the radially internal walls 5c, 6c of the first 5 and second arm 6 have a pair of axial retention teeth 14 facing each other and located at said inclined end walls 12, 13 in order to oppose the escape of the suture thread "S" housed in the slit 7.

In other words, the axial retaining teeth 14 define respective proximate edges 14a of the inclined walls 12, 13, wherein the axial slit 7 has minimal width (measured along the first direction).

Advantageously, in fact, the axial slit portion 7 interposed between the constrained ends 5a, 6a of the arms 5, 6 and the axial retaining teeth 14 has a width (along the first direction) greater than the distance between said teeth, each of which defines an abutment shoulder for the suture thread "A".

Preferably, further, the inclined end walls 12, 13, at least at said proximate edges 14a, have a complementary wavy pattern.

Advantageously, in this way even in the minimum width portion the slit 7 does not have a linear lumen, making an accidental axial escape of the suture thread "S" even more difficult, which to move away from the anchor 1 would have to assume precisely its wavy shape.

Preferably, further, with reference to an embodiment not illustrated, the main body 2 has a pair of longitudinal grooves branching off the constrained ends 5a, 6a of the first 5 and second arm 6, away from them. Such longitudinal grooves are thus made on the anchoring portion 3 of the main body 2 and define housing volumes of the suture thread sections "S" protruding from said slit 7.

Advantageously, in this way the suture thread "S" is completely housed in the radial dimension of the anchor, partly in the slit 7 and partly in the grooves, without positioning itself at any point between the anchor and the bone, a position in which it could be subject to breakage or wear.

The invention achieves its intended purposes and significant advantages are thus obtained.

In fact, the presence of transverse notches on the fork arms allows an axial retention of the thread which in their absence would be difficult, if not impossible.

Moreover, the arrangement of arms with reverse orientation (or in polar symmetry) causes the axial retention of the suture thread to be maximized.

Moreover, the introduction into the axial slit of a flared end section with retaining teeth permits once again prevention of the escape of the suture thread, a feature further maximized by the arrangement of wavy edges in a complementary manner at such retaining teeth.

The invention claimed is:

1. A bone anchor for a suture thread or ligament, comprising:
- a main body extending along a longitudinal axis and having a fork-shaped end portion, said end portion being provided with a first fork arm and a second fork arm, each fork arm extending between a constrained end and a free end and spaced from each other by an axial slit for receiving a suture thread or ligament,
- wherein the first fork arm and the second fork arm each have a circumferential notch defining, at the constrained end, a portion of reduced width so that the first fork arm and the second fork arm have, from the constrained end to the free end, an "L" or "J" conformation, wherein:
- the first fork arm and the second fork arm are arranged in polar symmetry with respect to the longitudinal axis, and the first fork arm and the second fork arm do not have reflectional symmetry relative to a plane that is disposed equidistant between an inner face of the first fork arm and an inner face of the second fork arm, wherein the inner faces face each other to delimit the axial slit.

2. The bone anchor according to claim 1, wherein said inner faces are provided with respective inclined end walls extending away from each other, so as to define a guide for the suture thread or ligament to fit in the slit.

3. The bone anchor according to claim 2, wherein said inner faces have a pair of axial retention teeth facing each other and located at said inclined end walls to oppose an exit of the suture thread or ligament housed in the slit.

4. The bone anchor according to claim 2, wherein said inclined end walls have, at least at respective adjacent edges, a complementary wavy pattern.

5. The bone anchor according to claim 1, wherein the main body comprises an anchoring portion having a peripheral profile provided with a plurality of gripping elements arranged in succession along said longitudinal axis.

6. The bone anchor according to claim 5, wherein said anchoring portion extends substantially cylindrically with a sawtooth peripheral profile.

7. A device for anchoring a suture thread or ligament to a bone, comprising:
- a handling member comprising a handle and a handling rod; and
- the bone anchor according to claim 1 removably attached to a free end of said handling rod.

* * * * *